United States Patent
Yoshizawa

(10) Patent No.: US 10,882,824 B2
(45) Date of Patent: Jan. 5, 2021

(54) METHOD FOR PURIFYING TRIFLUOROMETHYLPYRIDINES

(71) Applicant: ISHIHARA SANGYO KAISHA, LTD., Osaka (JP)

(72) Inventor: Hiroshi Yoshizawa, Osaka (JP)

(73) Assignee: ISHIHARA SANGYO KAISHA, LTD., Osaka (JP)

(*) Notice: Subject to any disclaimer, the term of this patent is extended or adjusted under 35 U.S.C. 154(b) by 0 days.

(21) Appl. No.: 16/499,665

(22) PCT Filed: Apr. 4, 2018

(86) PCT No.: PCT/JP2018/014497
§ 371 (c)(1),
(2) Date: Sep. 30, 2019

(87) PCT Pub. No.: WO2018/186460
PCT Pub. Date: Oct. 11, 2018

(65) Prior Publication Data
US 2020/0048203 A1  Feb. 13, 2020

(30) Foreign Application Priority Data
Apr. 4, 2017 (JP) .................. 2017-074229

(51) Int. Cl.
C07D 213/61 (2006.01)
C07B 63/04 (2006.01)

(52) U.S. Cl.
CPC ........... C07D 213/61 (2013.01); C07B 63/04 (2013.01)

(58) Field of Classification Search
CPC ........................... C07D 213/61; C07B 63/04
USPC ........................................... 546/345
See application file for complete search history.

(56) References Cited

U.S. PATENT DOCUMENTS

| | | | |
|---|---|---|---|
| 4,266,064 A | 5/1981 | Nishiyama et al. | |
| 4,288,599 A * | 9/1981 | Nishiyama | C07D 213/61 546/345 |
| 4,417,055 A * | 11/1983 | Nishiyama | C07D 213/61 546/345 |
| 4,490,534 A | 12/1984 | Fujikawa et al. | |
| 4,649,201 A * | 3/1987 | Friese | C07D 213/61 423/493 |
| 2016/0145211 A1* | 5/2016 | Andersen | C07D 213/74 546/300 |
| 2020/0048202 A1* | 2/2020 | Ando | C07D 213/26 |
| 2020/0102273 A1* | 4/2020 | Yu | C07D 213/61 |

FOREIGN PATENT DOCUMENTS

| | | | |
|---|---|---|---|
| CN | 1316423 A | | 10/2001 |
| CN | 102875454 A | | 1/2013 |
| CN | 106866510 | * | 6/2017 |
| CN | 108997203 | * | 12/2018 |
| GB | 2 045 245 A | | 10/1980 |
| JP | 55-22617 A | | 2/1980 |
| JP | 55-120564 A | | 9/1980 |
| JP | 55-147261 A | | 11/1980 |
| JP | 56-59757 A | | 5/1981 |
| JP | 56-97271 A | | 8/1981 |
| JP | 56-120667 A | | 9/1981 |
| JP | 57-159768 A | | 10/1982 |
| JP | 62-167766 A | | 7/1987 |
| JP | 2016-521730 A | | 7/2016 |

OTHER PUBLICATIONS

Chironna; "Wet scrubbing of acidic gases", APCMAG, 2011, 4 pages. (Year: 2011).*
International Search Report dated Jul. 3, 2018 issued by the International Searching Authority in counterpart International Application No. PCT/JP2018/014497 (PCT/ISA/210).
Written Opinion dated Jul. 3, 2018 issued by the International Searching Authority in counterpart International Application No. PCT/JP2018/014497 (PCT/ISA/237).
Extended European Search Report dated Oct. 30, 2020 in the corresponding European patent application No. 18781853.9.

* cited by examiner

Primary Examiner — Daniel R Carcanague
(74) Attorney, Agent, or Firm — Sughrue Mion, PLLC

(57) ABSTRACT

The present invention relates to a method for purifying a compound represented by the formula (I), the method including treating a mixture containing the compound represented by the formula (I) and a compound represented by the formula (II) with an aqueous solution of a basic compound.

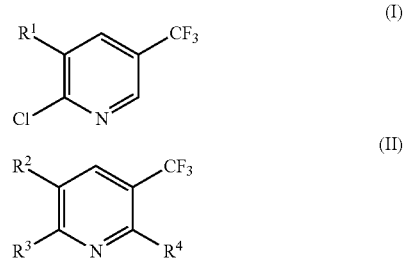

where, in the formula (I), $R^1$ represents a hydrogen atom or a chlorine atom; in the formula (II), $R^2$, $R^3$ and $R^4$ are the same or different from each other and represent a hydrogen, a chlorine atom or a fluorine atom independently, at least one of $R^3$ and $R^4$ represent a chlorine atom or a fluorine atom, and, in the case where $R^3$ represents a chlorine atom, $R^4$ represents a chlorine atom or a fluorine atom.

7 Claims, No Drawings

METHOD FOR PURIFYING TRIFLUOROMETHYLPYRIDINES

TECHNICAL FIELD

The present invention relates to a method for purifying trifluoromethylpyridines, specifically a method for purifying trifluoromethylpyridines including treatment with an aqueous solution of a basic compound.

BACKGROUND ART

Trifluoromethylpyridines, particularly trifluoromethylpyridines having a chlorine atom, are compounds useful as raw materials for medicines and agrochemicals (for example, herbicides, insecticides, fungicides, etc.).

As a method for producing trifluoromethylpyridines having a chlorine atom, for example, a method is known in which β-picolines is allowed to react with chlorine and anhydrous hydrogen fluoride in a vapor phase in the presence of a catalyst (Patent Documents 1 to 4). This method is industrially advantageous because trifluoromethylpyridines having a chlorine atom are obtained from the starting compounds in one step and in a short time.

RELATED ART

Patent Document

Patent Document 1: JP-A-55-120564
Patent Document 2: JP-A-55-147261
Patent Document 3: JP-A-56-59757
Patent Document 4: JP-A-56-120667

SUMMARY OF INVENTION

Problems to be Solved by the Invention

However, trifluoromethylpyridines obtained by the above method compose a mixture of a plurality of substances and, in order to use them as raw materials for medicines and agrochemicals, separation and purification operations are necessary.

For an industrial separation and purification method, one of example is distillation. However, in the case where boiling points of the substances contained in the mixture are close to each other, it may be difficult to obtain trifluoromethylpyridines having a purity required for use as raw materials for medicines and agrochemicals.

Therefore, in order to use trifluoromethylpyridines as raw materials for medicines and agrochemicals, a purification method capable of obtaining highly pure trifluoromethylpyridines containing the low content of impurities by a simple method that can be industrially carried out is required.

Means for Solving the Problems

As a result of investigations for solving the above problems, the present inventors have found that specific undesired substance(s) can be simply removed by treating a mixture of trifluoromethylpyridines having a chlorine atom with an aqueous solution of a basic compound, and they have accomplished the present invention.

Thus, the present invention relates to [1] to [9] below.

<1> A method for purifying a compound represented by the formula (I) comprising,
treating a mixture containing the compound represented by the formula (I):

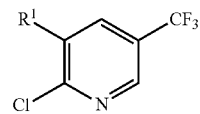

where $R^1$ represents a hydrogen atom or a chlorine atom, and a compound represented by the formula (II):

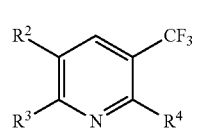

where $R^2$, $R^3$ and $R^4$ are the same or different from each other and represent a hydrogen, a chlorine atom or a fluorine atom independently, at least one of $R^3$ and $R^4$ represent a chlorine atom or a fluorine atom, and, in the case where $R^3$ represents a chlorine atom, $R^4$ represents a chlorine atom or a fluorine atom, with an aqueous solution of a basic compound.

<2> The purification method according to <1>,
wherein the compound represented by the formula (I) is represented by the formula (Ia):

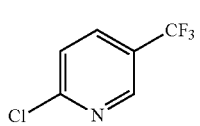

<3> The purification method according to <1>,
wherein the compound represented by the formula (I) is represented by the formula (Ib):

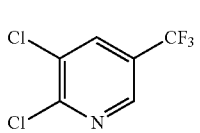

<4> The purification method according to any one of <1> to <3>,
wherein, in the formula (II), $R^2$ and $R^4$ are the same or different from each other and represent a hydrogen or a chlorine atom independently, and
$R^3$ represents a fluorine atom.

<5> The purification method according to any one of <1> to <4>,
wherein the basic compound is at least one selected from the group consisting of alkali metal hydroxides and alkali metal carbonates.

<6> The purification method according to any one of <1> to <4>,
wherein the basic compound is an alkali metal hydroxide.

<7> The purification method according to any one of <1> to <6>, wherein the concentration of the basic compound in the aqueous solution of the basic compound is from 40 to 50% by mass.

<8> The purification method according to any one of <1> to <7>,
wherein the treatment with the aqueous solution of the basic compound is performed at 60 to 110° C.

<9> The purification method according to any one of <1> to <8>,
wherein the mixture containing the compound represented by the formula (I) and the compound represented by the formula (II) is obtained by allowing a compound represented by the formula (A):

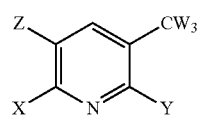
(A)

where Ws are the same or different from each other and represent a hydrogen, a fluorine atom or a chlorine atom independently, and X, Y and Z are the same or different from each other and represent a hydrogen or a chlorine atom independently,
to react with chlorine and/or anhydrous hydrogen fluoride in a vapor phase in the presence of a catalyst containing a halide of at least one metal element selected from the group consisting of aluminum, chromium, iron, nickel, manganese and cobalt, and a diluent.

Effects of the Invention

Based on the present invention, in a mixture containing a compound represented by the formula (I) and a compound represented by the formula (II), the content of the compound represented by the formula (II), which is an impurity, can be reduced by a simple method that can be industrially carried out and thus the compound represented by the formula (I) useful as a raw material for medicines and agrochemicals can be purified.

EMBODIMENTS FOR CARRYING OUT THE INVENTION

1. Method for Purifying Compound Represented by Formula (I)

The purification method of the present invention includes treating a mixture containing a compound represented by the formula (I) useful as a raw material for medicines and agrochemicals, a compound represented by the formula (II), which is an impurity, and optionally a further other compound, with an aqueous solution of a basic compound.

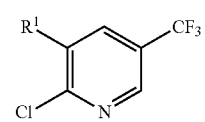
(I)

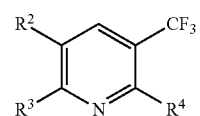
(II)

wherein, in the formula (I), $R^1$ represents a hydrogen atom or a chlorine atom; in the formula (II), $R^2$, $R^3$ and $R^4$ are the same or different from each other and represent a hydrogen, a chlorine atom or a fluorine atom independently, at least one of $R^3$ and $R^4$ represent a chlorine atom or a fluorine atom, and, in the case where $R^3$ represents a chlorine atom, $R^4$ represents a chlorine atom or a fluorine atom.

Specifically, the compound represented by the formula (I) in the present invention is preferably a compound represented by the formula (Ia) (2-chloro-5-trifluoromethylpyridine) or a compound represented by the formula (Ib) (2,3-dichloro-5-trifluoromethylpyridine).

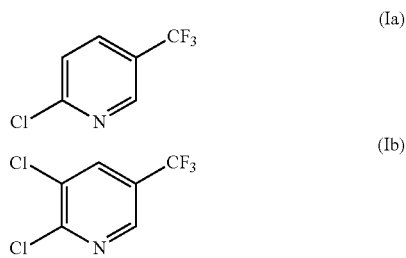

In the present invention, a mixture to be treated with an aqueous solution of a basic compound (hereinafter, also simply referred to as mixture) contains, in addition to the compound represented by the formula (I), the compound represented by the formula (II) and optionally, a further other compound as an impurity.

As the mixture, a mixture obtained by a production method in accordance with the production methods described in Patent Documents 1 to 4, more specifically by the production method to be mentioned later may be suitably used. However, the mixture is not limited thereto and, for example, a mixture obtained by the other method can be also used. Moreover, as the mixture, a mixture obtained by purifying a product obtained by the production method to be mentioned later, by means of a purification method known in the art (for example, filtration, distillation, extraction, recrystallization, chromatography, etc.) may be used.

When the compound represented by the formula (I) is represented by the formula (Ia), the compound represented by the formula (II), which may be contained as an impurity, includes but not limited to:

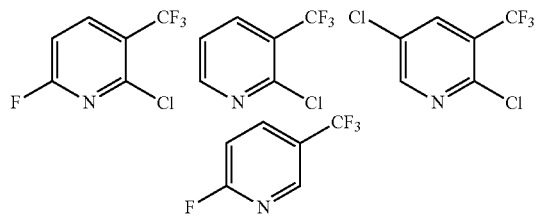

and the like.

When the compound represented by the formula (I) is represented by the formula (Ia), the other compound, which may be contained as an impurity, includes but not limited to:

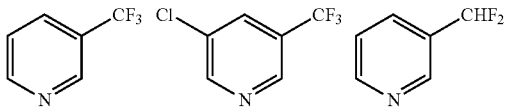

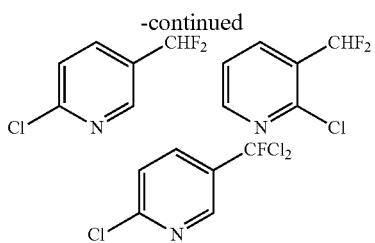

and the like.

When the compound represented by the formula (I) is represented by the formula (Ib), the compound represented by the formula (II), which may be contained as an impurity, includes but not limited to:

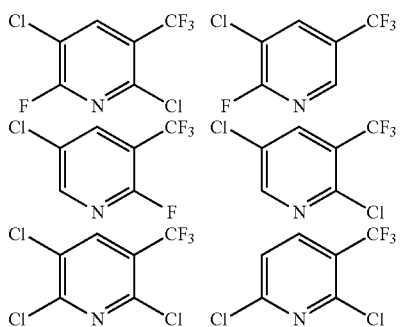

and the like.

When the compound represented by the formula (I) is represented by the formula (Ib), the other compound, which may be contained as an impurity, includes but not limited to:

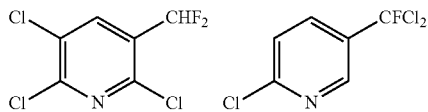

and the like.

When the compound represented by the formula (I) is used as a raw material for medicines and agrochemicals, the content of impurities in the mixture may be required to be 0.1% by mass or less. For example, when trifluoromethylpyridines having a chlorine atom are produced in accordance with the production method to be described later or the production methods described in Patent Documents 1 to 4, the trifluoromethylpyridines contain about 0.1 to 50% by mass of the compound represented by the formula (II) and other compounds as impurities, and if necessary, purification is carried out by distillation or the like. Preferably, the application of the present invention to the mixture obtained by purification by distillation or the like allows the content of the impurities to be 0.1% by mass or less.

The present invention includes treating a mixture containing the compound represented by the formula (I) and the compound represented by the formula (II) with an aqueous solution of a basic compound.

The "treating with an aqueous solution of a basic compound" means heating while stirring after the aqueous solution of a basic compound is charged.

The stirring time may be appropriately selected according to the type and concentration of the basic compound to be used and the reaction temperature, and is usually 0.1 to 24 hours, preferably 1 to 12 hours.

The heating can be carried out usually at 60 to 110° C., preferably at 80 to 100° C.

Alternatively, the stirring and heating can be also finished at the time when the content of the compound represented by the formula (II), which is an impurity, becomes equal to or less than a predetermined amount using a known analysis method (for example, high performance liquid chromatography, gas chromatography, or the like).

The basic compound in the present invention includes but not particularly limited to alkali metal hydroxides and alkali metal carbonates.

Specifically, the alkali metal hydroxides include sodium hydroxide and potassium hydroxide, and the alkali metal carbonates include sodium carbonate and potassium carbonate. Among them, alkali metal hydroxides such as sodium hydroxide and potassium hydroxide are preferable.

In the present invention, the concentration of the basic compound in the aqueous solution of the basic compound may be appropriately selected according to the basic compound to be used, but it is usually from 10 to 50% by mass, preferably from 40 to 50% by mass.

The amount of the aqueous solution of the basic compound to be used may be selected according to the content of the compound represented by the formula (II) contained in the mixture, but it is usually from 0.1 to 20% by mass, preferably from 3 to 5% by mass based on the mixture.

In the present invention, the compound represented by the formula (II) is decomposed by the treatment with the aqueous solution of the basic compound to form a more hydrophilic decomposed product. Thus, after completion of the treatment with the aqueous solution of the basic compound, by washing with water, warm water or the like and separating the resulting product as necessary, the decomposed product of the compound represented by the formula (II) is removed to the aqueous phase side. Thus, the compound represented by the formula (I) can be more easily purified.

For example, when the compound represented by the formula (II) is a compound in which $R^2$ and $R^4$ are the same or different from each other and represent a hydrogen or a chlorine atom independently and $R^3$ represents a fluorine atom (for example, the compounds shown below), the boiling point of the compound is close to the boiling point of the compound represented by the formula (I). Hence, it is difficult to separate and remove the compound by a commonly-used purification means such as distillation. Even in such a case, the treatment with the aqueous solution of the basic compound allows the compounds shown below to become highly hydrophilic decomposed products in which the fluorine atom at the a position is converted into a hydroxyl group, and the products are removed to the aqueous phase side. Thus, the compound represented by the formula (I) can be more easily purified.

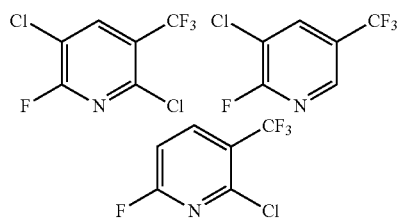

2. Method for Producing Mixture Containing Compound Represented by Formula (I) and Compound Represented by Formula (II)

In the present invention, a mixture to be treated with an aqueous solution of a basic compound is not particularly limited to the specific mixture as long as it contains the compound represented by the formula (I) and the compound represented by the formula (II). Preferably, the mixture is a mixture obtained by a method in accordance with the production methods described in Patent Documents 1 to 4, that is, a method of allowing β-picolines represented by the formula (A) to react with chlorine and/or anhydrous hydrogen fluoride in a vapor phase in the presence of a catalyst and a diluent. Hereinafter, the production method will be described in detail.

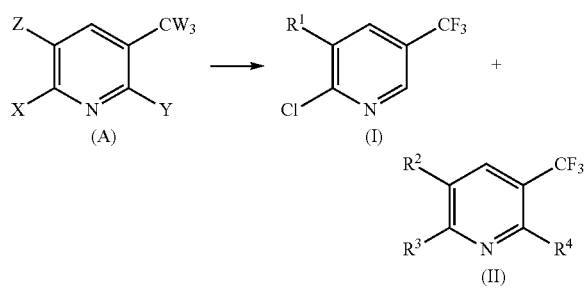

where, in the formula (A), Ws are the same or different from each other and represent a hydrogen, a fluorine atom or a chlorine atom independently, and X, Y and Z are the same or different from each other and represent a hydrogen or a chlorine atom independently; in the formula (I), $R^1$ represents the same as described above; in the formula (II), $R^2$, $R^3$ and $R^4$ represents the same as described above.

The mixture of the compound represented by the formula (I) and the compound represented by the formula (II) obtained by this production method may further contain various compounds as described above as impurities.

β-picolines represented by the formula (A) include β-picoline, 2-chloro-β-picoline and 6-chloro-β-picoline.

In particular, for producing the compound represented by the formula (Ia), it is advantageous to use β-picoline which is easily available as a raw material.

Moreover, for producing the compound represented by the formula (Ib), a compound represented by the formula (A) in which X represents a chlorine atom, both Z and Y represent a hydrogen, and $CW_3$ is $CF_3$ (2-chloro-5-trifluoromethylpyridine, i.e., the compound represented by the formula (Ia)) as a raw material may be used.

The catalyst includes a catalyst including a halide of at least one metal element selected from the group consisting of aluminum, chromium, iron, nickel, manganese and cobalt.

More specifically, the above-described halide includes hydrated aluminum trifluoride ($AlF_3 \cdot 3H_2O$), aluminum trifluoride ($AlF_3$), hydrated chromium trifluoride ($CrF_3 \cdot 3H_2O$), chromium trifluoride ($CrF_3$), hydrated ferrous fluoride ($FeF_2 \cdot 8H_2O$), ferrous fluoride ($FeF_2$), ferric fluoride ($FeF_3$), ferrous chloride ($FeCl_2$), ferric chloride ($FeCl_3$), hydrated nickel(II) fluoride ($NiF_2 \cdot 3H_2O$), nickel(III) fluoride ($NiF_3$), manganese(II) fluoride ($MnF_2$), manganese(III) fluoride ($MnF_3$), manganese tetrafluoride ($MnF_4$), and cobalt(II) fluoride ($CoF_2$), cobalt(III) fluoride ($CoF_3$).

The amount of the catalyst to be used is not categorically determined as it depends on the reaction conditions, but is usually from 0.01 to 3 mol based on 1 mol of the compound represented by the formula (A), which is a raw material.

Usually, the catalyst is mixed with a carrier such as active carbon or active alumina to be formed into particles or pellets of an appropriate size, and then the resulting one is allowed to be present as a fixed bed or a fluidized bed. Moreover, when a fluoride is used as the catalyst, the catalyst may be directly introduced into a reaction tube and allowed to be present in the form of a fluoride of the metal element described above. Industrially, it is advantageous to use a method in which the metal element is charged into a reaction tube in the form of an oxide, a chloride or a carbonate salt and then is allowed to be present after the reaction with anhydrous hydrogen fluoride to convert into a fluoride thereof.

As the diluent, for example, organic solvents of halogenated hydrocarbons such as carbon tetrachloride, chloroform, methylene chloride, F-112 ($CFCl_2$—$CFCl_2$) and F-113 ($CF_2Cl$—$CFCl_2$) and inert gases such as nitrogen, helium and argon can be used. These diluents have a function of suppressing combustion, carbonization, formation of tar-like by-products and the like. The amount of the diluent to be used is usually from 2 to 70 mol based on 1 mol of the compound represented by the formula (A).

The amounts of chlorine and anhydrous hydrogen fluoride to be used are not categorically determined as it depends on the kind of the compound represented by the formula (A), which is a raw material, the kind of the target substance, the reactor, and the like. However, the amounts are usually from 2 to 15 mol and 2 to 60 mol, respectively, based on 1 mol of the compound represented by the formula (A).

In the present production method, the compound represented by the formula (A), the diluent, and chlorine and/or anhydrous hydrogen fluoride may be separately supplied to a reactor, or may be supplied as a mixture thereof. Moreover, these can also be supplied simultaneously or sequentially, or collectively or dividedly.

The reaction temperature is usually from 200 to 600° C., and the residence time of the reaction mixture in the reaction zone is usually from 3 to 60 seconds. The formation rate of trifluoromethylpyridines having a chlorine atom is usually 90% or more.

Usually, from the reactor, gaseous substance containing a product containing the compound represented by the formula (I) as a main component, the compound represented by the formula (II), intermediate products, hydrogen chloride, unreacted hydrogen fluoride and chlorine, and the diluent are discharged, and through an appropriate cooling and condensing equipment, the reaction products are obtained as a liquid mixture. When intermediate products are contained in the obtained liquid mixture, these intermediate products may be separated and recovered together with the unreacted raw material or the diluent, and if necessary, may be dechlorinated by reduction according to a conventional method. Then, the intermediate products can be recycled to the reaction zone as the compounds represented by the formula (A).

The obtained mixture containing the compound represented by the formula (I), the compound represented by the formula (II) which is an impurity, and optionally a further other compound may be subjected to the purification method of the present invention as it is. Preferably, a mixture obtained through further purification by a purification method known in the art (for example, filtration, distillation, extraction, recrystallization, chromatography, etc.) is subjected to the purification method of the present invention.

EXAMPLES

The following describes Examples of the present invention but the invention should not be construed as being limited thereto.

The abbreviations used in the following Examples are as follows.
DCTF: 2,3-dichloro-5-trifluoromethylpyridine
DCFTF: 2,5-dichloro-6-fluoro-3-hifluoromethylpyridine
56CFTF: 5-chloro-6-fluoro-3-trifluoromethylpyridine
CTF: 2-chloro-5-trifluoromethylpyridine
26CFTF: 2-chloro-6-fluoro-3-trifluoromethylpyridine
2-CTF: 2-chloro-3-trifluoromethylpyridine
2,6-DCTF: 2,6-dichloro-3-trifluoromethylpyridine
256TCTF: 2,5,6-trichloro-3-trifluoromethylpyridine
NaOH: sodium hydroxide
GC: gas chromatography
HPLC: high performance liquid chromatography Purification Example 1

A crude DCTF mixture (7,500 kg (5 m$^3$)) was charged into a jacketed tank (10 m$^3$) equipped with a stirrer made of SUS. Next, a 48% by mass aqueous NaOH solution (300 kg) which corresponds to 4% by mass relative to the mass of the crude DCTF mixture was charged. Then, the whole was heated and stirred at 80° C. for 8 hours.

After confirming that the peak area ratio (Peak area %) of DCFTF was 0.1 PA % or less by GC analysis under the following measurement conditions, warm water (3,750 kg) at 60° C. was charged and followed by stirring for 30 minutes. The mixture was cooled to 50° C. and allowed to stand for 30 minutes, and liquid separation was conducted to obtain purified DCTF.

The term "crude DCTF mixture" means a mixture containing DCTF, DCFTF and 56CFTF.

Purification Example 2

A crude DCTF mixture (7,500 kg (5 m$^3$)) was charged into a jacketed tank (10 m$^3$) equipped with a stirrer made of SUS. Next, a 48% by mass aqueous NaOH solution (450 kg) which corresponds to 6% by mass relative to the mass of the crude DCTF mixture was charged. Then, the whole was heated and stirred at 80° C. for 5 hours.

After confirming that the peak area ratio of DCFTF was 0.1 PA % or less by GC analysis under the following measurement conditions, post treatment was performed in accordance with Purification Example 1 to obtain purified DCTF.

Purification Example 3

A crude DCTF mixture (7,500 kg (5 m$^3$)) was charged into a jacketed tank (10 m$^3$) equipped with a stirrer made of SUS. Next, a 48% by mass aqueous NaOH solution (450 kg), which corresponds to 6% by mass relative to the mass of the crude DCTF mixture, was charged. Then, the whole was heated and stirred at 90° C. for 2 hours.

After confirming that the peak area ratio of DCFTF was 0.1 PA % or less by GC analysis under the following measurement conditions, post treatment was performed in accordance with Purification Example 1 to obtain purified DCTF.

Purification Example 4

A crude DCTF mixture (150 g) was charged into a reactor equipped with a stirrer. Next, a 48% by mass aqueous NaOH solution which corresponds to 12.5% by mass relative to the mass of the crude DCTF mixture was charged. Then, the whole was heated and stirred at 80° C. for 11 hours.

After confirming that the peak area ratio of DCFTF was 0.1 PA % or less by GC analysis under the following measurement conditions, post treatment was performed in accordance with Purification Example 1 to obtain purified DCTF.

The results of the GC analysis for purification examples 1 to 4 are shown in Table 1. The measurement conditions of GC were as follows.
Column: 3.2 mm ID×3.1 mL 10% silicon OV-101 chromosorb WHP 80 to 100 mesh or its equivalent
Carrier: dichloromethane
Column temperature: 100° C.
Flow rate: about 140 kPa
Detector: FID

TABLE 1

| Purification | Before treatment with aqueous NaOH solution (PA %) | | | After treatment with aqueous NaOH solution (PA %) | | |
|---|---|---|---|---|---|---|
| Example | DCTF | DCFTF | 56CFTF | DCTF | DCFTF | 56CFTF |
| 1 | 70.42 | 0.26 | 1.61 | 72.08 | 0.02 | 0.52 |
| 2 | 63.75 | 0.52 | 1.88 | 65.13 | 0.01 | 0.22 |
| 3 | 64.53 | 0.17 | 0.83 | 64.87 | 0.01 | 0.15 |
| 4 | 98.58 | 0.89 | — | 99.71 | 0 | — |

Purification Example 5

A crude CTF mixture (300 g, CTF: 98 PA % or more) was charged into a round bottom flask (1 L), and then a 25% by mass aqueous solution of NaOH (15 g) which corresponds to 5% by mass relative to the mass of the crude CTF mixture was charged. The mixture was heated and stirred at 100° C. for 15 minutes.

As a result of analysis by HPLC under the following measurement conditions, the peak area ratio of 26CFTF in the crude CTF mixture was 0.307 PA %, but after the treatment, was halved to 0.167 PA %. In order to control the peak area ratio of 26CFTF to 0.1 PA % or less, the treatment time may be further prolonged.

The term "crude CTF mixture" means a mixture containing CTF and 26 CFTF.

Moreover, the measurement conditions of HPLC were as follows.
Column: Cosmosil-5C18ARII or its equivalent
Column temperature: equivalent to 40° C.
Carrier: Acetonitrile: Water (10 mM H$_3$PO$_4$)=60:40
Flow rate: 1.2 mL/min
Detection: UV (254 nm)

Production Examples of CTF and DCTF

Production Example (1)

As a reactor, an Inconel-made vertical reaction tube having a catalyst fluidized bed whose reaction portion had an inner diameter of 97.1 mm and a height of 1,570 mm was installed, which connected with two Inconel-made preheating tubes having an inner diameter of 30 mm and a length of 1,000 mm was used for raw materials and an inert diluent, and the reaction tube and the preheating tubes were covered with an electric heater and a heat-insulating material so that temperature could be controlled.

One obtained by impregnating 2.2 kg of aluminum trifluoride having a particle diameter of 105 to 250 μm with 277 g of anhydrous ferric chloride was placed in the catalyst packing part and heated to 200° C., and an anhydrous hydrogen fluoride was introduced at a rate of 2.3 L/minute for 1 hour to activate the catalyst.

The reactor was heated to 400° C., β-picoline and nitrogen gas were introduced through the preheating tube so as to be rates of 6.8 g/minute and 9.9 L/minute, respectively, as a mixed gas of about 200° C. and chlorine gas and anhydrous hydrogen fluoride were introduced through a preheating tube so as to be rates of 7.4 L/minute and 7.4 L/minute, respectively, as a mixed gas of about 200° C. They were allowed to react for about 30 hours. During the time, the activated catalyst was continuously supplied and discharged at a rate of 300 g/hour. The residence time of the reaction mixture in the tube was about 3.4 seconds.

A gas discharged from the reactor was allowed to pass through a water-washing column and an alkali-washing column, a condensation product was separated and neutralized with an aqueous ammonia solution, and 19.11 kg of an oily substance was obtained by steam distillation. The oily substance contains about 1 PA % of DCFTF and about 2 PA % of 56 CFTF.

The oily substance was distilled to obtain 1.53 kg of a first fraction containing β-trifluoromethylpyridine as a main component, 9.56 kg of a main fraction containing CTF as a main component, and 7.62 kg of a post fraction. The post fraction contained 3.7 PA % of CTF, 14.5 PA % of 2-CTF, 47.7 PA % of 2,6-DCTF and 34.1 PA % of others.

Production Example (2)

In the above Production Example (1), the reaction was carried out in the same manner except that β-picoline, β-trifluoromethylpyridine, chlorine gas and anhydrous hydrogen fluoride were introduced at rates of 4.6 g/minute, 3.4 g/minute, 5.8 L/minute, and 5 L/minute, respectively. The residence time of the reaction mixture was about 4 seconds and the reaction was continuously carried out for about 8 hours. The reaction product was similarly post-treated to obtain 5.47 kg of an oily substance.

The main composition of this oily substance was 8.2 PA % of β-trifluoromethylpyridine, 57.8 PA % of CTF, 9.5 PA % of 2-CTF, 16.1 PA % of DCTF and 8.4 PA % of others.

By distilling the oily substance, a fraction containing CTF as a main component can be obtained.

Production Example (3)

As a reactor, one where the reaction portion was an Inconel-made vertical reaction tube having a catalyst fluidized bed having an inner diameter of 30 mm and a height of 500 mm, which connected with two Inconel-made preheating tubes having an inner diameter of 20 mm and a length of 300 mm, and these were covered with an electric heater and a heat insulating material so that temperature could be controlled, was used.

One (60 g) obtained by mixing a solution in which 24 g of ferric chloride was dissolved in 200 ml of ethanol and 120 g of active carbon (80 to 200 meshes) and then drying them was introduced into the catalyst packing part of the reactor and heated to about 200° C. Then, chlorine gas was introduced so as to be a rate of 1.3 L/minute for about 3 hours to activate the catalyst.

A mixed gas of CTF and nitrogen gas were preheated to about 200 to 250° C. and introduced through one preheating tube so that the rate of the former be 0.5 g/minute and the rate of the latter be 1.0 L/minute into the reaction tube. Also, a mixed gas of chlorine gas and nitrogen gas preheated to the same temperature was introduced through another preheating tube so that the rate of the former be 0.25 L/minute and the rate of the latter be 0.6 L/minute into the reaction tube. They were allowed to react at 250° C. for about 4 hours.

A gas discharged from the reactor was allowed to pass through a water-washing column and an alkali-washing column and condensed, and an oily substance was separated and collected and, after washed with water, dried over sodium sulfate to obtain 110 g of an oily substance.

The main composition of this oily substance was 74.1 PA % of DCTF, 7.1 PA % of 256TCTF, 16.0 PA % of CTF, and 2.7 PA % of others.

By distilling the oily substance, a fraction containing DCTF as a main component can be obtained.

While the invention has been described in detail and with reference to specific embodiments thereof, it will be apparent to one skilled in the art that various changes and modifications can be made therein without departing from the spirit and scope thereof. The present application is based on Japanese Patent Application No. 2017-74229 filed on Apr. 4, 2017, and the contents are incorporated herein by reference.

The invention claimed is:

1. A method for purifying a compound represented by the formula (I) comprising,
treating a mixture containing the compound represented by the formula (I):

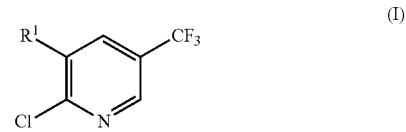

where $R^1$ represents a hydrogen atom or a chlorine atom, and
a compound represented by the formula (II):

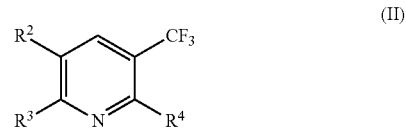

where $R^2$, $R^3$ and $R^4$ are the same or different from each other and represent a hydrogen, a chlorine atom or a fluorine atom independently, at least one of $R^3$ and $R^4$ represent a chlorine atom or a fluorine atom, and, in the case where $R^3$ represents a chlorine atom, $R^4$ represents a chlorine atom or a fluorine atom,
with an aqueous solution of a basic compound,
wherein the concentration of the basic compound in the aqueous solution of the basic compound is from 40 to 50% by mass, and
the treatment with the aqueous solution of the basic compound is performed at 60 to 110° C.

2. The purification method according to claim 1, wherein the compound represented by the formula (I) is represented by the formula (Ia):

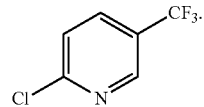

(Ia)

3. The purification method according to claim 1, wherein the compound represented by the formula (I) is represented by the formula (Ib):

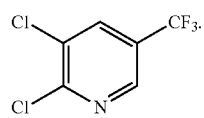

(Ib)

4. The purification method according to claim 1, wherein, in the formula (II), $R^2$ and $R^4$ are the same or different from each other and represent a hydrogen or a chlorine atom independently, and $R^3$ represents a fluorine atom.

5. The purification method according to claim 1, to react with chlorine and/or anhydrous hydrogen fluoride in a vapor phase in the presence of a catalyst containing a halide of at least one metal element selected from the group consisting of aluminum, chromium, iron, nickel, manganese and cobalt, and a diluent.

6. The purification method according to claim 1, wherein the basic compound is an alkali metal hydroxide.

7. The purification method according to claim 1, wherein the mixture containing the compound represented by the formula (I) and the compound represented by the formula (II) is obtained by allowing a compound represented by the formula (A):

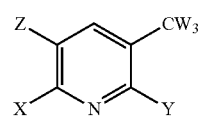

(A)

where Ws are the same or different from each other and represent a hydrogen, a fluorine atom or a chlorine atom independently, and X, Y and Z are the same or different from each other and represent a hydrogen or a chlorine atom independently,
the treatment with the aqueous solution of the basic compound is performed at 60 to 110° C.

* * * * *